United States Patent
Ewing et al.

(10) Patent No.: US 6,437,201 B1
(45) Date of Patent: *Aug. 20, 2002

(54) PRODUCTION OF HYDROFLUOROALKANES

(75) Inventors: Paul Nicholas Ewing, Warrington; Richard Llewellyn Powell, Tarporley; Michael Anthony Davies, Runcorn; Christopher John Skinner, Newton Hall, all of (GB)

(73) Assignee: Ineos Fluor Holdings Limited, South Hampton (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,735
(22) PCT Filed: Oct. 23, 1995
(86) PCT No.: PCT/GB95/02491
§ 371 (c)(1),
(2), (4) Date: Apr. 24, 1997
(87) PCT Pub. No.: WO95/02491
PCT Pub. Date: Nov. 12, 1992

(30) Foreign Application Priority Data

Oct. 27, 1994 (GB) .............................................. 9421619
Dec. 22, 1994 (GB) .............................................. 9425929

(51) Int. Cl.$^7$ .............................................. C07C 17/08
(52) U.S. Cl. ...................... 570/169; 570/165; 570/166; 570/167; 570/168

(58) Field of Search .............................. 570/169, 165, 570/166, 167, 168

(56) References Cited

U.S. PATENT DOCUMENTS

| | | | | |
|---|---|---|---|---|
| 4,129,603 A | * | 12/1978 | Bell | ........................... 570/169 |
| 5,045,634 A | | 9/1991 | Fernandez et al. | |

FOREIGN PATENT DOCUMENTS

| | | | | |
|---|---|---|---|---|
| DE | 1246703 | * | 8/1967 | ................. 570/169 |
| EP | 0 537 560 | | 4/1993 | |
| GB | 901297 | * | 7/1962 | ................. 570/169 |
| GB | 901 297 | | 7/1962 | |
| WO | 92 19576 | | 11/1992 | |
| WO | 92/19576 | * | 11/1992 | ................. 570/169 |

* cited by examiner

*Primary Examiner*—Alan Siegel
(74) *Attorney, Agent, or Firm*—Cook, Alex, McFarron, Manzo, Cummings & Mehler, Ltd.

(57) ABSTRACT

An improved process for the manufacture of $CF_3CHF_2$ by contacting 1,2-dichloro-1,1,2-trifluoroethane ($CClF_2CHClF$) or 1-chloro-1,1,2,2-tetrafluoroethane ($CHF_2CClF_2$) or mixtures of $CF_3CHCl_2$ and $CClF_2CHClF$ or mixtures of $CF_3CHClF$ and $CHF_2CClF_2$ with HF in the presence of a $Cr_2O_3$ catalyst prepared by pyrolysis of ammonium dichromate, the reaction being conducted under controlled conditions whereby the production of $CF_3CHF_2$ is maximized, and the formation of chloropentafluoroethane ($CF_3CClF_2$) and other perhalo derivatives is minimized. The subject hydrogen-containing compound is useful as a blowing agent, propellant, refrigerant, fire extinguishing agent, or sterilant carrier gas.

23 Claims, No Drawings

PRODUCTION OF HYDROFLUOROALKANES

This invention relates to a process for the production of hydrofluoroalkanes, particularly 1,1,1,2-tetrafluoroethane and pentafluoroethane.

Several processes have been proposed for the production of 1,1,1,2-tetrafluoroethane, otherwise known as HFC 134a, and pentafluoroethane, otherwise known as HFC 125 which are employed as or as components of replacements for chlorofluorocarbons in the many applications in which chlorofluorocarbons are employed. Amongst such processes is the fluorination of the corresponding chlorine-containing starting material by reacting the starting material with hydrogen fluoride in the liquid or the vapour phase, usually in the presence of a fluorination catalyst.

Thus it has been proposed in United Kingdom Patent Specification No. 1,589,924 to produce HFC 134a by the vapour phase fluorination of 1,1,1-trifluoro-2-chloroethane (HCFC 133a) which is itself obtainable by the fluorination of trichloroethylene as described in United Kingdom Patent Specification No. 1,307,224.

The formation of HFC 134a as a minor product of the fluorination of trichloroethylene is described in United Kingdom Patent Specification No 819,849, the major reaction product being HCFC 133a.

More recently, processes for the production of HFC 134a from trichloroethylene based on a combination of the reaction of trichloroethylene with hydrogen fluoride to produce HCFC 133a and the reaction of HCFC 133a with hydrogen fluoride to produce HFC 134a have been proposed.

In WO 90/08755, the contents of which are incorporated herein by reference, there is described the conversion of trichloroethylene to HFC 134a wherein the two reactions steps are carried out in a single reaction zone with recycle of part of the product stream containing HCFC 133a.

In EP 0 449 614, the contents of which are also incorporated herein by reference, there is described a process for the manufacture of HFC 134a which comprises the steps of:

(A) contacting a mixture of trichloroethylene and hydrogen fluoride with a fluorination catalyst under superatmospheric pressure at a temperature in the range from about 200° C. to about 400° C. in a first reaction zone to form a product containing 1,1,1-trifluoro-2-chloroethane and hydrogen chloride together with unreacted starting materials, (B) passing product of step A together with hydrogen fluoride to a second reaction zone containing a fluorination catalyst at a temperature in the range from about 280° C. to about 450° C. but higher than the temperature in step A to form a product containing 1,1,1-trifluoro-2-chloroethane, 1,1,1,2-tetrafluoroethane and hydrogen chloride, (C) treating product of step B to separate 1,1,1,2-tetrafluoroethane and hydrogen chloride from 1,1,1-trifluoro-2-chloroethane and unreacted hydrogen fluoride, and (D) feeding 1,1,1-trifluoro-2-chloroethane obtained from step C together with trichloroethylene and hydrogen fluoride to said first reaction zone (step A).

In EP 0 449 617, the contents of which are also incorporated herein by reference, there is described a process for the production of BFC 134a which comprises the steps of:

(A) contacting a mixture of 1,1,1-trifluoro-2-chloroethane and hydrogen fluoride with a fluorination catalyst at a temperature in the range from about 280° C. to about 450° C. in a first reaction zone to form a product containing 1,1,1,2-tetrafluoroethane and hydrogen chloride together with unreacted starting materials, (B) passing product of step A together with trichloroethylene to a second reaction zone containing a fluorination catalyst at a temperature in the range from about 200° C. to about 400° C. but lower than the temperature in step A to form a product containing 1,1,1-trifluoro-2-chloroethane, 1,1,1,2-tetrafluoroethane, hydrogen chloride and unreacted trichloroethylene and hydrogen fluoride, (C) treating product of step B to separate 1,1,1,2-tetrafluoroethane and hydrogen chloride from 1,1,1-trifluoro-2-chloroethane, unreacted trichloroethylene and hydrogen fluoride, and (D) feeding 1,1,1-trifluoro-2-chloroethane obtained from step C together with hydrogen fluoride to said first reaction zone (step A).

However, a problem which is encountered with processes for the production of 1,1,1,2-tetrafluoroethane based on the hydrofluorination of 1-chloro-2,2,2-trifluoroethane and/or trichloroethylene, is that the conversion of 1-chloro-2,2,2-trifluoroethane to 1,1,1,2-tetrafluoroethane is equilibrium limited, there being a maximum conversion of 1-chloro-2,2,2-trifluoroethane to 1,1,1,2-tetrafluoroethane of only about 20% under typical operating conditions.

It has also been proposed to produce pentafluoroethane (HFC 125) by the catalysed fluorination with hydrogen fluoride of chlorotetrafluoroethane (HCFC 124) and/or dichlorotrifluoroethane (HCFC 123) which are themselves obtainable by the fluorination of perchloroethylene with hydrogen fluoride.

The present invention resides in a process for the production of hydrofluoroalkanes, particularly 1,1,1,2-tetrafluoroethane and pentafluoroethane from hitherto unused starting materials, which process in the case of production of 1,1,1,2-tetrafluoroethane is not subject to the aforementioned equilibrium limitation problem.

According to the present invention there is provided a process for the production of a hydrofluoroalkane which comprises contacting a hydrochlorofluoroethane having the formula CClXYCFHZ or a(hydro)chlorofluoroethene having the formula CClA=CFZ in which X and Y are each independently chlorine or fluorine, Z is chlorine or hydrogen and A is chlorine or fluorine provided that where each of X and Y is fluorine then Z is hydrogen in the vapour phase with hydrogen fluoride and a fluorination catalyst and recovering a hydrofluoroalkane from the resulting products.

In a particular embodiment of the process for producing 1,1,1,2-tetrafluoroethane, the hydrochlorofluoroethane has the formula CClXYCFH$_2$ and the (hydro)chlorofluoroethene has the formula CClA=CFH.

We have found that the product gases from the process for producing 1,1,1,2-tetrafluoroethane comprise a greater molar proportion of 1,1,1,2-tetrafluoroethane than is obtained when 1-chloro-2,2,2-trifluoroethane is used as the starting material.

The starting materials for the process are CCl$_3$CFH$_2$, CCl$_2$FCFH$_2$, CClF$_2$CFH$_2$, CCl$_2$FCClFH, CCl$_3$CHFCl, CCl$_2$=CFH, CClF=CFH, CCl$_2$=CFCl and CClF=CFCl. We prefer to employ CCl$_2$=CFH or CCl$_2$FCFH$_2$, especially CCl$_2$=CFH for the production of 1,1,1,2-tetrafluoroethane and CCl$_2$FCClFH or CClF=CFCl for the production of pentafluoroethane since these materials are more readily available.

Processes for the production of the starting materials of the present invention are known. Thus for example $CCl_2$=CFH may be produced from trichloroethylene, as described in the Journal of Organic Chemistry 28, 112 (1963), or from tetrachloroethane as described in EP 537560.

Suitable fluorination catalysts are those which yield the desired hydrofluoroalkane as a product of the reaction with a yield of greater than 20%, preferably greater than 25%, based on the starting material processed and include catalysts based on chromia or chromium oxyfluoride, and the fluorides or oxyfluorides of other metals, for example magnesium and aluminium. Activity promoting amounts of other metals, for example zinc and nickel may also be present; we particularly prefer to employ a catalyst comprising zinc on chromia as described fully in published European Patent Application No. 502605, the contents of which are incorporated herein by reference.

The relative proportion of hydrogen fluoride to starting material which is employed may vary within wide limits although it is generally preferred to employ a stoichiometric excess of hydrogen fluoride. The stoichiometrically required molar ratio depends upon the particular starting material. Where the starting material is the preferred 1,1-dichloro-2-fluoroethene, the stoichiometrically required molar ratio of hydrogen fluoride to 1,1-dichloro-2-fluoroethene is 3:1. The molar ratio of hydrogen fluoride to the starting material, for example 1,1-dichloro-2-fluoroethene, will usually be at least 2:1, and preferably is at least 4:1 and especially at least 6:1 and substantially greater excesses of hydrogen fluoride, for example up to 50:1, may be employed if desired.

The temperature at which the process is carried out is preferably at least 180° C. and more preferably at least 200° C. or 220° C. but may be significantly lower than the temperatures typically employed for the conversion of 1-chloro-2,2,2-trifluoroethane to 1,1,1,2-tetrafluoroethane. Preferably the temperature is not greater than 350° C., especially not greater than 330° C.

The process may be carried out at atmospheric pressure although superatmospheric pressure, say up to about 30 bar is preferred.

The contact time is preferably in the range from about 0.1 seconds to about 10 seconds, preferably in the range from about 0.5 seconds to about 5 seconds at atmospheric pressure.

As described previously, hydrofluorination of trichloroethylene via the intermediate 1-chloro-2,2,2-trifluoroethane is used for the production of 1,1,1,2-tetrafluoroethane. If desired the process of the present invention may be combined with processes for the production of 1,1,1,2-tetrafluoroethane based on trichloroethylene/1-chloro-2,2,2-trifluoroethane, Thus and according to a preferred embodiment of the invention, a hydrochlorofluoroalkane and/or a(hydro) chlorofluoroalkene as hereinbefore defined, for example 1,1-dichloro-2-fluoroethene is fed as a second starting material to processes for the production of 1,1,1,2-tetrafluoroethane employing trichloroethylene as the starting material.

The co-feeding of trichloroethylene and the second starting material such as 1,1-dichloro-2-fluoroethene may be effected in the processes described in our published European Patent Applications Nos 0 449 617, and 0 449 614, the contents of which are incorporated herein by reference.

The invention is illustrated but not limited by the following Examples.

The 1,1-dichloro-2-fluoroethene (HCFC 1121a) used in the Examples was synthesised via the ethanolic potassium hydroxide dehydrochlorination of trichlorofluoroethane (HCFC 131) as described in J. Am. Chem. Soc., 1936, 58, 402. The resulting crude product was washed with water, dried with magnesium sulphate and then fractionally distilled with the fraction boiling between 32° C. and 34° C. being collected; this fraction was analysed and found to be pure HCFC 1121a.

The 1,1-dichloro-1,2-difluoroethane (HCFC 132c) used in the Examples was synthesised by oxyfluorination of 1,1-dichloroethane (vinylidene chloride) using lead (IV) oxide in anhydrous hydrogen fluoride as described in J. Am. Chem. Soc., 1945, 67, 1639. The reaction was carried out in a Hastalloy C autoclave and yielded a considerable amount of the co-product 1,1-dichloro-1-fluoroethane (HCFC 141b). The resulting reaction mixture was fractionally distilled and a fraction comprising 60% HCFC 141b and 40% HCFC 132c by weight was collected; it was not feasible to separate the HCFC 132c from the HCFC 141b by distillation.

The 1,1,2-trichloro-1,2-difluoroethane (HCFC 122a) used in the Examples was synthesised by oxyfluorination of trichloroethylene using lead (IV) oxide in anhydrous hydrogen fluoride as described in J. Am. Chem. Soc., 1945, 67, 1639 in a Hastalloy C autoclave. The reaction mixture contained unreacted trichloroethylene which was removed by treatment with bromine to form 1,2-dibromo-1,1,2-trichloroethane followed by fractional distillation. A fraction comprising HCFC 122a was collected and analysis showed it to be pure HCFC 122a.

EXAMPLE 1

2 ml of a catalyst comprising 8% by weight of zinc on chromia was charged to a ¼" I.D. Inconel reactor tube and the catalyst was pre-fluorinated by passing hydrogen fluoride over the catalyst at 300° C. for 24 hours. After this time, hydrogen fluoride and 1,1-dichloro-2-fluoroethene (in ethanol) were passed over the catalyst at 275° C. and at flow rates of 25 ml/minute and 6 ml/minute respectively giving a contact time with the catalyst of 1.4 seconds.

The reactor off-gases were sampled and the samples analysed by Gas Chromatography. The conversion of 1,1-dichloro-2-fluoroethene was 55.8% and selectivity to 1,1,1,2-tetrafluoroethane was 67.6% respectively.

EXAMPLE 2

2.5 gm of a catalyst comprising 8% by weight of zinc on chromia was charged to a ¼" I.D. Inconel reactor tube and the catalyst was dried at 300° C. for 1 hour in a stream of 10 ml/minute of nitrogen gas. The dried catalyst was then fluorinated by heating at 300° C. for 2 hours in a stream of 10 ml/minute of hydrogen fluoride and nitrogen delivering approximately 41 m mole of hydrogen fluoride per hour.

A sample of 1,1-dichloro-2-fluoroethene (0.64 gm) in hydrogen fluoride previously prepared by introducing the 1,1-dichloro-2-fluoroethene into a hydrogen fluoride purged Whitey bomb and comprising a mole ratio of hydrogen fluoride: sample of 8:1 was fed over the catalyst by diverting the hydrogen fluoride/nitrogen flow, the catalyst temperature being maintained throughout at 300° C. The mole ratio of hydrogen fluoride: 1,1-dichloro-2-fluoroethene in the flow was approximately 4:1.

After a period of 5 minutes from diversion of the hydrogen fluoride/nitrogen flow to entrain the sample of 1,1-dichloro-2-fluoroethene, samples of the products stream, after scrubbing with sodium carbonate solution, were analyzed by Gas Chromatography analysis and IR spectroscopy analysis.

Analysis determined that the major products were 1,1,1,2-tetrafluoroethane [HFC 134a], chloro-2,2,2-trifluoroethane [HFC 133a] and chlorotetrafluoroethane [HCFC 124].

The results are shown in Table 1 and show that feeding 1,1-dichloro-2-fluoroethene instead of trichloroethylene produces a higher yield of 1,1,1,2-tetrafluoroethane (HFC 134a) and is not subject to the equilibrium restriction which is encountered using trichloroethylene as the feed.

EXAMPLE 3

The procedure described in Example 2 was repeated except that the flow of hydrogen fluoride/nitrogen was reduced to 5 ml/minute instead of 10 ml/minute so that the mole ratio of hydrogen fluoride: 1,1-dichloro-2-fluoroethene in the feed to the catalyst was halved to approximately 2:1.

Analysis showed that the major products were 1,1,1,2-tetrafluoroethane (HFC 134a) and chloro-2,2,2-trifluoroethane (HFC 133a) in approximately equal amounts. The results are shown in Table 1.

EXAMPLE 4

The procedure described in Example 2 was repeated to react 1,1-dichloro-2-fluoroethene (0.32 g) with hydrogen fluoride at different catalyst temperatures. The initial mole ratio of hydrogen fluoride: 1,1,-dichloro-2-fluoroethene fed to the catalyst was approximately 8:1

Three runs were carried out at catalyst temperatures of 250° C., 300° C. and 350° C. during the sample feed. Samples of the product streams for analysis were taken after 4 minutes from diversion of the hydrogen fluoridelnitrogen flow to entrain the sample. The results of analysis are shown in Table 1.

At 250° C., the conversion of 1,1-dichloro-2-fluoroethene was 42.9% and 1,1,1,2-tetrafluoroethane was the only major product.

At 300° C., the conversion of 1,1-dichloro-2-fluoroethene was 81.6% and the major product was again 1,1,1,2-tetrafluoroethane although a significant amount of chloro-2,2,2-trifluoroethane [HCFC 133a] was also obtained.

At 350° C., the conversion of 1,1,-dichloro-2-fluoroethene was 98.5% and the major products were 1,1,1,2-tetrafluoroethane and chloro-2,2,2-trifluoroethane in a ratio of approximately 1:2.

TABLE 1

| Example | | | Selectivity (%) | |
| --- | --- | --- | --- | --- |
| No. | Temp. (° C.) | Conversion (%) | 134a | 133a |
| 2 | 300 | 93.7 | 54.8 | 37.2 |
| 3 | 300 | 86.6 | 48.2 | 46.0 |
| 4 | 250 | 42.9 | 76.5 | 5.3 |
|   | 300 | 81.6 | 69.3 | 25.3 |
|   | 350 | 98.5 | 32.8 | 65.5 |

EXAMPLE 5

This example describes the conversion of 1,1-dichloro-1,2-difluoroethane (HCFC 132c) to 1,1,1,2-tetrafluoroethane.

The procedure described in Example 2 was used to react 1,1-dichloro-1,2-difluoroethane (0.3 g) with hydrogen fluoride at a range of catalyst temperatures from 200° C. to 333° C. Samples for analysis were taken after 4 minutes. Runs were carried out at catalyst temperatures of 200° C., 250° C., 290° C. and 330° C. The sample of 1,1-dichloro-1,2-difluoroethane was prepared as described hereinbefore and contained 60% by weight of 1,1-dichloro-1-fluoroethane (HCFC 141b) and 40% by weight of HCFC 132c.

The major product observed in each run was 1,1,1-trifluoroethane (HFC 143a). It is assumed in interpreting the results that (a) this major product is derived exclusively from the 1,1-dichloro-1-fluoroethane in the starting material and (b) the 1,1-dichloro-1-fluoroethane plays no other part in the process so that all products other than 1,1,1-trifluoroethane are derived from the 1,1-dichloro-1,2-difluoroethane.

The analysis results are shown in Table 2.

At 330° C., the conversion of 1,1-dichloro-1,2-difluoroethane was 100% and the major products were 1,1,1,2-tetrafluoroethane and chloro-2,2,2-trifluoroethane.

At 290° C., the conversion was 100% with 1,1,1,2-tetrafluoroethane and chloro-2,2,2-trifluoroethane being the major products.

At 250° C., the conversion was 100% with 1,1,1,2-tetrafluoroethane and chloro-2,2,2-trifluoroethane being the major products.

At 200° C., the conversion was 100% with 1,1,1,2-tetrafluoroethane being the major product.

It was observed in these runs that 1,1-dichloro-2-fluoroethene (HCFC 1121a) was obtained as a by product with % selectivities of 16.2% (at 330° C.), 2.9% (at 290° C.), 31.7% (at 250° C.) and 55.6% (at 200° C.). It was also observed that 1-chloro-2,2,2-trifluoroethane (HCFC 133b) was obtained at 250° C. (5.1%) and at 200° C. (23.6%).

TABLE 2

| Example | | | Selectivity (%) | |
| --- | --- | --- | --- | --- |
| No. | Temp. (° C.) | Conversion (%) | 134a | 133a |
| 5 | 200 | 100 | 17.2 | 1.3 |
|   | 250 | 100 | 54.8 | 6.2 |
|   | 290 | 100 | 26.9 | 65.0 |
|   | 330 | 100 | 22.5 | 52.6 |

COMPARATIVE EXAMPLE

For purposes of comparison, the procedure described in Example 2 was used to react chloro-2,2,2-trifluoroethane (HCFC 133a) (0.3 gm) with hydrogen fluoride at catalyst temperatures of 290° C. (Run 1) and 330° C. (Run 2).

In Run 1, at 290° C., the conversion of HCFC 133a was only about 7% and the yield of 1,1,1,2-tetrafluoroethane was 6.5%.

In Run 2, at 330° C., the conversion of HCFC was about 20% and the yield of 1,1,1,2-tetrafluoroethane was 18.7%.

The results are shown in Table 3.

TABLE 3

| Example No. | Temp. (° C.) | Conversion (%) [of 133a] | Selectivity (%) [of 134a] |
| --- | --- | --- | --- |
| Comparative Example | 290 | 7.2 | 90.3 |
|   | 330 | 19.8 | 94.4 |

EXAMPLE 6

This example illustrates the conversion of 1,1,2-trichloro-1,2-difluoroethane (HCFC 122a) to pentafluoroethane (HFC 125). The procedure described in Example 2 was used to react 1,1,2-trichloro-1,2-difluoroethane (0.47 gm) with hydrogen fluoride at a catalyst temperature of 340° C. except that the catalyst was fluorinated overnight instead of for 2 hours. The results are shown in Table 4.

TABLE 4

| Example | | | Selectivity (%) | | | |
|---|---|---|---|---|---|---|
| No. | Temp. (° C.) | Conversion (%) | 125 | 123/a | 124/a | 1111 |
| 6 | 340 | 100 | 33.2 | 2.1 | 29.6 | 7.4 |

What is claimed is:

1. A process for the production of 1,1,1,2-tetrafluoroethane which comprises contacting a hydrochlorofluoroethane having the formula $CClXYCFH_2$ or a hydrochlorofluoroethene having the formula $CClA=CFH$ in which X and Y are each independently chlorine or fluorine and A is chlorine or fluorine, in the vapour phase with hydrogen fluoride and a fluorination catalyst and recovering 1,1,1,2-tetrafluoroethane from the resulting products.

2. A process as claimed in claim 1 wherein the hydrogen fluoride is present in stoichiometric excess relative to the hydrochlorofluoroethane or hydrochlorofluoroethene.

3. A process as claimed in claim 2 wherein the molar ratio of hydrogen fluoride to the hydrochlorofluoroethane or hydrochlorofluoroethene is at least 4:1.

4. A process as claimed in claim 1 wherein the molar ratio of hydrogen fluoride to the (hydro)chlorofluoroethene is at least 4:1.

5. A process as claimed in claim 1 wherein the temperature is from 180° C. to 350° C.

6. A process as claimed in claim 1 which is carried out under superatmospheric pressure.

7. A process as claimed in claim 1 wherein the fluorination catalyst is based on chromia or chromium oxyfluoride or the fluorides and oxyfluorides of other metals.

8. A process as claimed in claim 1 wherein the hydrochlorofluoroethene is $CCl_2=CFH$.

9. A process as claimed in claim 1 wherein the hydrochlorofluoroethane or hydrochlorofluoroethene is fed as a second starting material together with trichloroethylene.

10. A process for the production of 1,1,1,2-tetrafluoroethane which comprises contacting a hydrochlorofluoroethene having the formula $CClA=CFH$ in which A is chlorine or fluorine, in the vapour phase with hydrogen fluoride and a fluorination catalyst and recovering 1,1,1,2-tetrafluoroethane from the resulting products.

11. A process as claimed in claim 10 wherein the hydrogen fluoride is present in stoichiometric excess relative to the hydrochlorofluoroethene.

12. A process as claimed in claim 10 wherein the contacting is carried out at a temperature from 180° C. to 350° C.

13. A process as claimed in claim 10 which is carried out under superatmospheric pressure.

14. A process as claimed in claim 10 wherein the fluorination catalyst is based on chromia or chromium oxyfluoride or the fluorides and oxyfluorides of other metals.

15. A process for the production of 1,1,1,2-tetrafluoroethane comprising:
   a) contacting, at a temperature of 180° C. to 300° C., a hydrochlorofluoroethane having the formula $CClXYCFH_2$ or a hydrochlorofluoroethene having the formula $CClA=CFH$ in which X and Y are each independently chlorine or fluorine, and A is chlorine or fluorine, in the vapour phase with hydrogen fluoride and a fluorination catalyst; and
   b) recovering 1,1,1,2-tetrafluoroethane from the resulting products.

16. A process as claimed in claim 15 wherein the hydrogen fluoride is present in stoichiometric excess relative to the hydrochlorofluoroethane or hydrochlorofluoroethene.

17. A process as claimed in claim 15 wherein the molar ratio of hydrogen fluoride to the hydrochlorofluoroethane or hydrochlorofluoroethene is at least 4:1.

18. A process as claimed in claim 15 which is carried out under superatmospheric pressure.

19. A process as claimed in claim 15 wherein the fluorination catalyst is based on chromia or chromium oxyfluoride or the fluorides and oxyfluorides of other metals.

20. A process as claimed in claim 15 wherein the hydrochlorofluoroethene is $CCl_2=CFH$.

21. A process as claimed in claim 15 wherein the hydrochlorofluoroethane or hydrochlorofluoroethene is fed as a second starting material together with trichloroethylene.

22. The process as claimed in claim 5 wherein the temperature is 300° C. or less.

23. The process as claimed in claim 12, wherein the temperature is 300° C. or less.

* * * * *